United States Patent [19]
Bakke

[11] Patent Number: 6,035,102
[45] Date of Patent: Mar. 7, 2000

[54] CYLINDRICAL ELECTRIC LIQUID WARMING SYSTEM UTILIZING HEATING BY CONDENSATION

[76] Inventor: Allan P. Bakke, 3220 Countyview Ct., S.W., Rochester, Minn. 55902

[21] Appl. No.: 09/032,535

[22] Filed: Feb. 27, 1998

[51] Int. Cl.[7] .............. A61F 7/00; A61F 7/12; F28F 7/00
[52] U.S. Cl. .............. 392/470; 165/46; 604/113
[58] Field of Search .............. 392/470; 165/46; 604/113, 114

[56] References Cited

U.S. PATENT DOCUMENTS

| | | | |
|---|---|---|---|
| 1,838,026 | 12/1931 | Williams | 604/114 |
| 1,982,213 | 11/1934 | Hopkins | 219/38 |
| 1,987,119 | 1/1935 | Long | 219/39 |
| 3,682,089 | 8/1972 | Unger et al. | 99/281 |
| 4,019,020 | 4/1977 | Bilbee et al. | 392/470 |
| 4,272,667 | 6/1981 | Golowacz | 219/326 |
| 4,314,143 | 2/1982 | Bilstad et al. | 219/497 |
| 4,464,563 | 8/1984 | Jewett | 219/298 |
| 4,602,146 | 7/1986 | Barns et al. | 219/373 |
| 4,707,587 | 11/1987 | Greenblatt | 219/299 |
| 5,013,889 | 5/1991 | Bakke | 392/470 |
| 5,245,683 | 9/1993 | Ford et al. | 392/470 |
| 5,420,962 | 5/1995 | Bakke | 392/470 |
| 5,846,224 | 12/1998 | Sword et al. | 604/113 |

OTHER PUBLICATIONS

Baxter ThermaCyl Blood/Fluid Warmer Brochure—1997.
American Medical Systems DW 1000 Blood/Fluid Warmer Brochure 1983.

*Primary Examiner*—John A. Jeffery
*Assistant Examiner*—Daniel L. Robinson
*Attorney, Agent, or Firm*—Burd, Bartz & Gutenkauf

[57] ABSTRACT

A system for warming blood or other liquids to body temperature and maintaining the liquid at that temperature for infusion into a patient. The system is characterized by a cylindrical condensation liquid heating chamber having an inner tubular air heater. A cylindrical heat retaining shell surrounds and is spaced from the outer wall of the heating chamber. A flat flexible heat exchanging liquid warming envelope is held clamped between the outer wall of the heating chamber and the surrounding shell. An external outer elongated air hose is connected at one end to a warmed air outlet from the air heater and extends to the patient and surrounds an inner elongated warm liquid flow line to maintain the temperature of the liquid.

16 Claims, 4 Drawing Sheets

CYLINDRICAL ELECTRIC LIQUID WARMING SYSTEM UTILIZING HEATING BY CONDENSATION

BACKGROUND OF THE INVENTION

1. Field of the Invention

This invention relates to a system for warming blood and other liquids to physiologic temperature before infusion into a patient. The system is characterized by an external cylindrical heating surface around which is wrapped a flat disposable heat exchanging liquid warming envelope with automatic gas bubble venting and by an internal cylindrical heating surface with radial air warming fins for the provision of active warm air insulation of the intravenous line to the patient.

Blood is stored at approximately 4 degrees C. prior to transfusion and should be warmed to physiologic temperature of about 35 to 40 degrees C. for transfusion. Infusion of cold liquids at high flow rates can cause cardiac arrhythmias, cardiac arrest and death. Even at low flow rates it is desirable to warm intravenous liquids for delivery to the patient, especially if the patient is an infant or child, has cardiac disease or is otherwise of fragile health.

In the intravenous administration of blood products and other intravenous liquids, it is necessary that the liquid being administered to the patient be free of entrained air or other gas bubbles to prevent venous gas embolism and its potentially fatal consequences. The present system is designed to deliver warmed liquids from very low flow rates to high flow rates of 500 ml/min or more. At high flow rates significant volumes of gas bubbles are generated during the warming process. These must be removed before administration of the liquid to the patient.

2. Prior Art

My prior U.S. Pat. No. 5,013,889 is directed to an electric blood warmer utilizing heating by vapor condensation. My prior U.S. Pat. No. 5,420,962 is directed to a convection blood warming system having an automatic hydrophobic vent incorporated in the disposable flattened tube plastic heat exchanging envelope and utilizing active warm air insulation of the intravenous line to the patient. The disclosure of those patents are incorporated herein by reference.

One commercially available blood warmer (Baxter ThermaCyl Blood/Fluid Warmer) employs an external nearly cylindrical (actually conical) heating surface. Another (American Medical Systems DW 1000 blood/fluid warmer) utilizes a cylindrical heating surface. Both include conventional electrical convective heating units and flexible plastic film cuffs through which the blood flows. Neither includes air heating means.

One object of the present invention is to provide the increased constant heating surface temperature characteristic of heating by vapor condensation. Another object of the present invention is to utilize an internal cylindrical heating surface extended by fins for air warming to actively insulate the intravenous line to the patient.

SUMMARY OF THE INVENTION

Broadly stated, the present invention is directed to a system for warming blood or other liquids to body temperature and maintaining the liquid at that temperature for infusion into a patient. The system includes a closed elongated annular cylindrical condensation heating chamber with an outer cylindrical heat exchanging wall and an inner spaced apart tubular heat exchanging wall. A cylindrical heat retaining shell surrounds and is spaced from the outer wall of the heating chamber. A flat flexible heat exchanging liquid warming envelope is held clamped between the outer wall of the heating chamber and the surrounding shell. The space within the inner heat exchanging wall constitutes a tubular air heating unit which includes a cool air inlet at one end of the unit, a plurality of heat transfer fins extending radially inward from the inner tubular wall and a fan for conducting air from the inlet past the fins. An external outer elongated air hose is connected at one end to a warmed air outlet from the air heating unit and extends to the patient. This air hose is adapted to receive an inner elongated liquid flow line therein to maintain the temperature of the liquid in the flow line.

BRIEF DESCRIPTION OF THE DRAWINGS

The invention is illustrated by the accompanying drawings in which corresponding parts are identified by the same numerals and in which.

DETAILED DESCRIPTION OF THE PREFERRED EMBODIMENT

Figure 1:
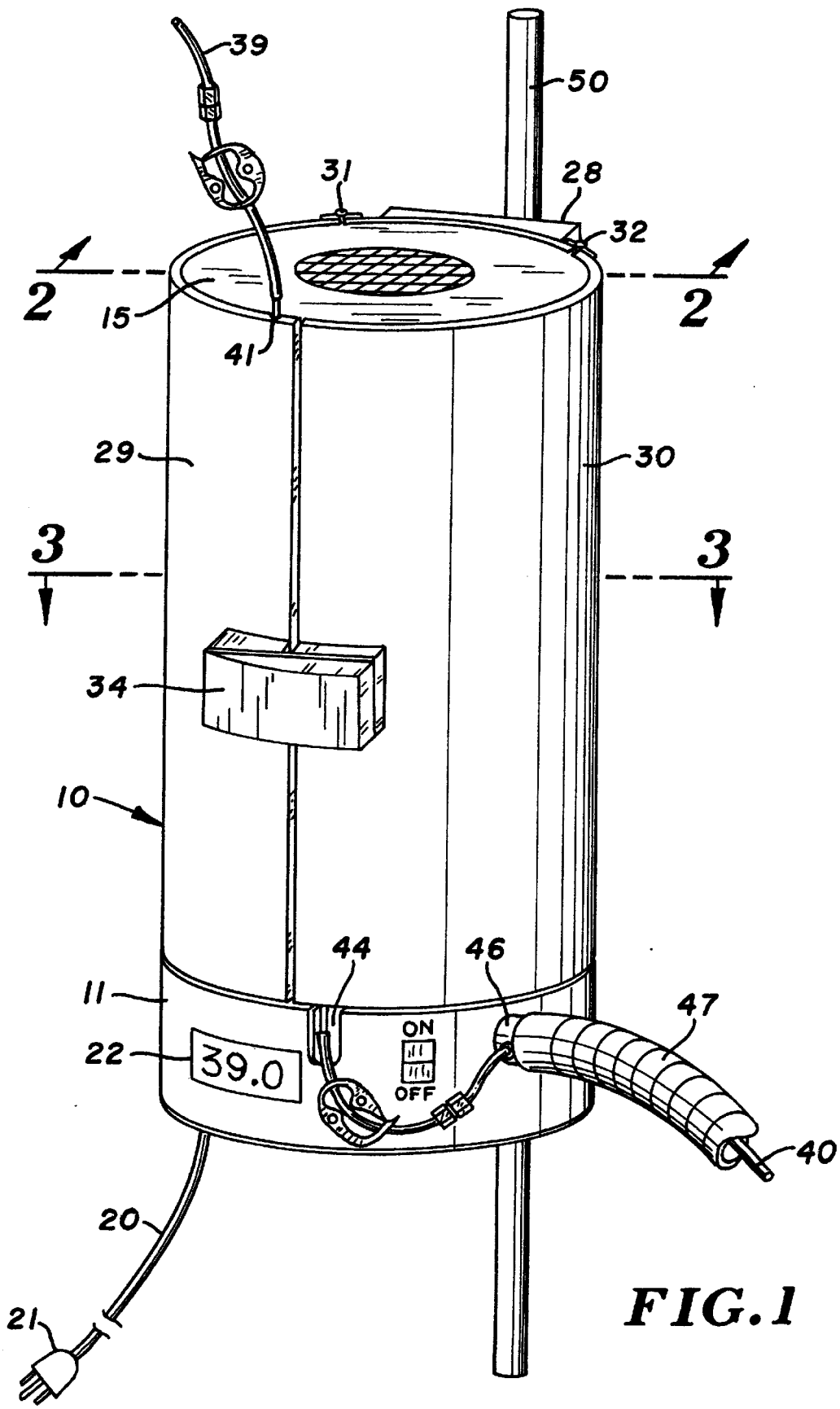
FIG. 1 is an isometric view of the liquid warming system according to the present invention incorporating an electrically heated liquid warmer utilizing heating by condensation.
Figure 2:
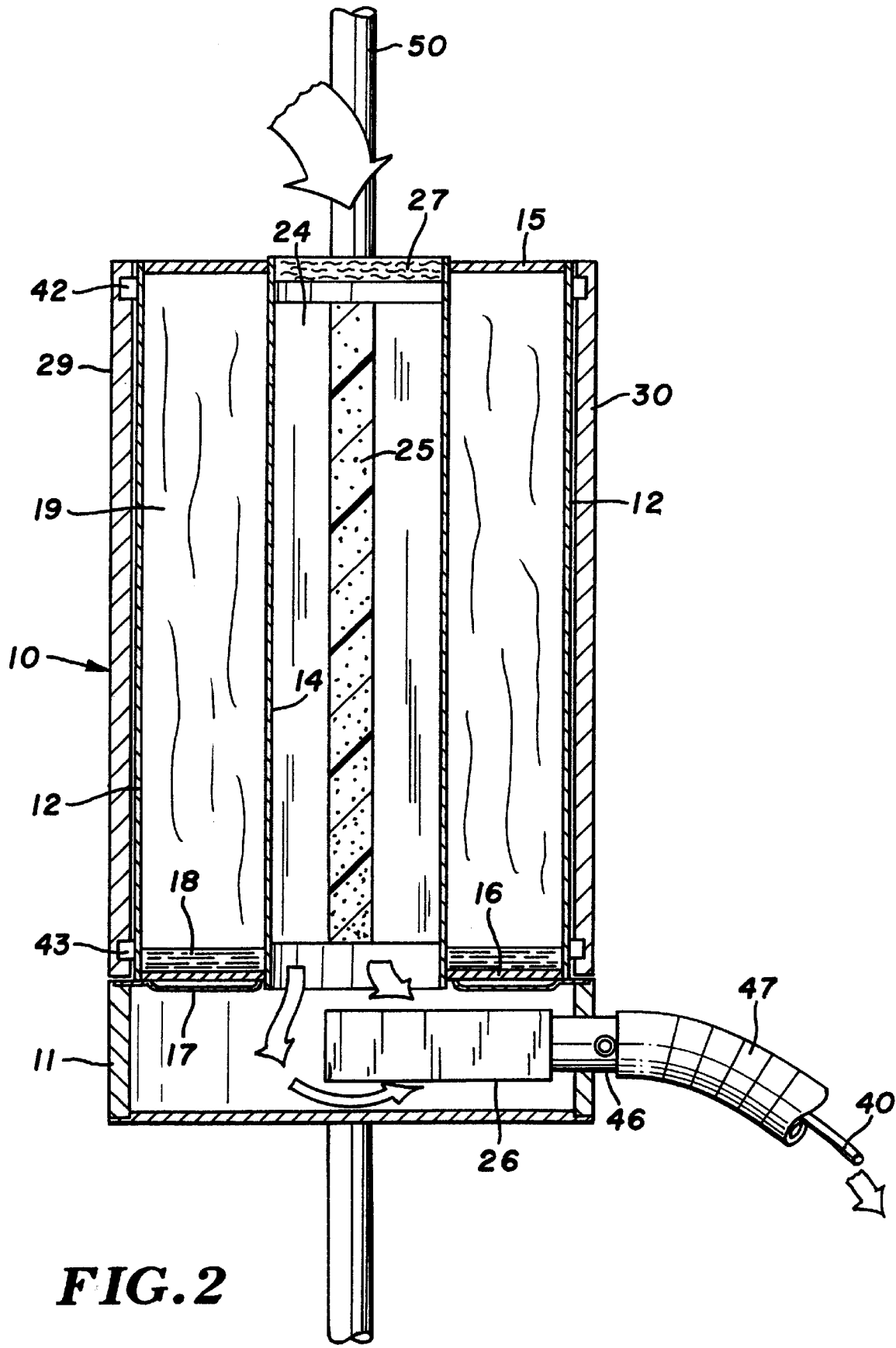
FIG. 2 is a vertical section along the line 2—2 of FIG. 1 and in the direction of the arrows.
Figure 3:
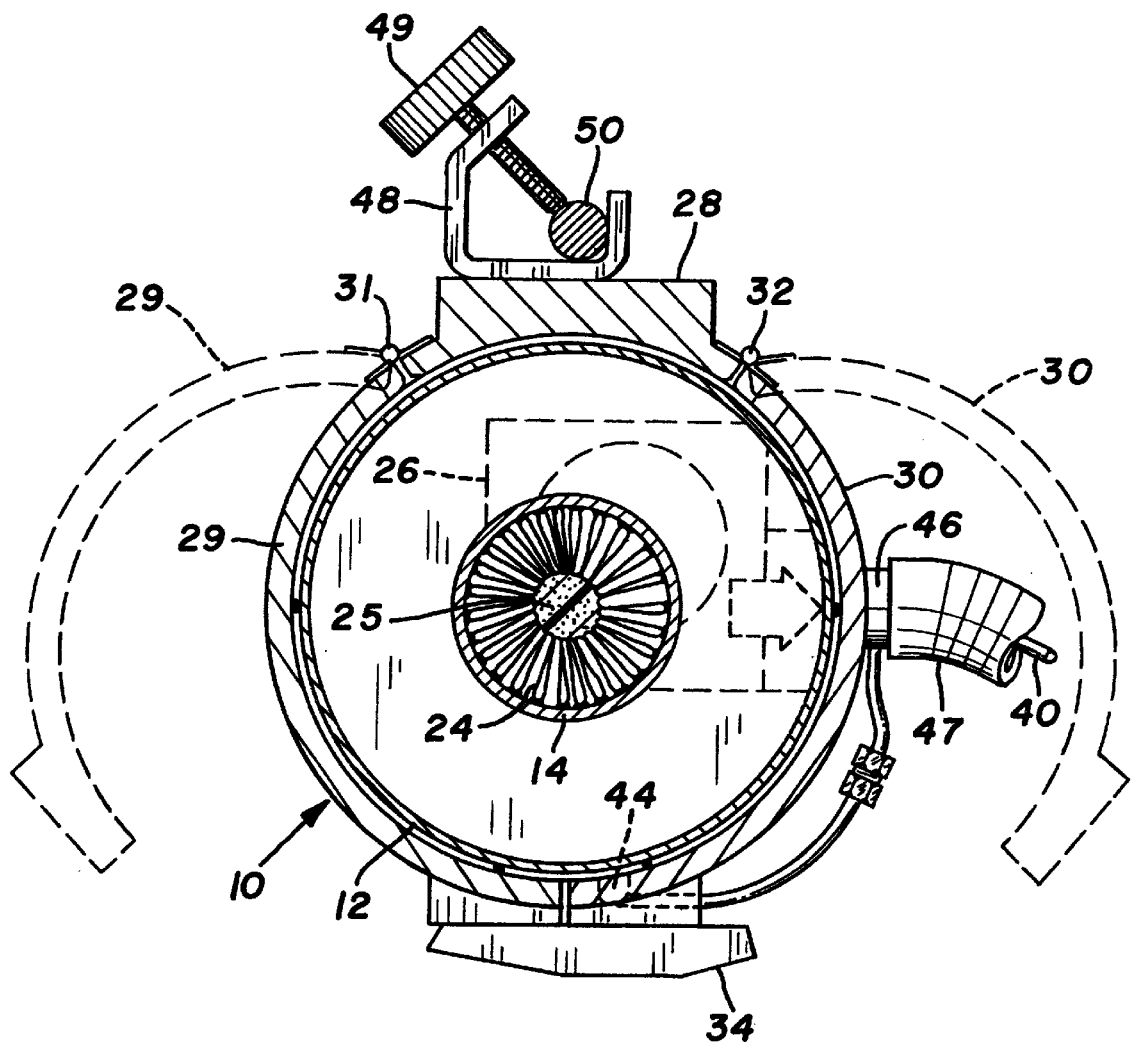
FIG. 3 is a horizontal section on the line 3—3 of FIG. 1 and in the direction of the arrows.

Referring now to the drawings, and particularly to FIGS. 1–3, there is disclosed a liquid warming apparatus indicated generally at 10. The apparatus includes a base housing 11. A condensation heating unit is supported above housing 11 and comprises a cylindrical outer wall 12 forming an external heating surface and a concentric inner cylindrical wall 14 forming an inner heating surface. The space between the inner and outer cylindrical walls is hermetically sealed by annular top and bottom plates 15 and 16 which are welded, brazed or soldered in place. An electric etched foil heater element 17 is fixed to the bottom surface of bottom plate 16. A water reservoir 18 is maintained in the bottom of the heater unit. When heated the water from reservoir 18 evaporates to produce steam 19 throughout the heating unit. The heater is connected through wire 20 and plug 21 to any convenient electrical outlet. The external heating surface of wall 12 is preferably maintained at about 40° C. The temperature is controlled by a solid state temperature controller 22 utilizing a thermistor sensor in contact with the external heating surface.

A plurality of radially inwardly extending air warming metal fins 24 are brazed or otherwise secured on the inner surface of the inner cylindrical heating surface of tubular wall 14. A central core 25 of a flow blocking material, such as flexible polyurethane foam, is located within the inner edges of fins 24 to insure contact with the heating fin surfaces of air blown through the central passage within the heating unit. Ambient cool air is drawn into the heater by fan 26 through filter 27 generally in the path shown by the arrows and is connectively warmed as it passes over the fins 24, which are heated by condensation of steam on the vapor side of the inner cylindrical heating surface of heating wall 14.

As seen in FIG. 3, a housing back wall 28, having an arcuate inner surface, extends vertically upwardly from the housing base 11 spaced a short distance from outer heating wall 12. A pair of semi-cylindrical arcuate heat retaining and envelope restraining doors 29 and 30 are hinged at 31 and 32, respectively, to the opposite edges of the housing back wall 28. Doors 29 and 30 may be swung outwardly to permit installation of a disposable heat exchanging envelope 33 around the outer cylindrical heating unit wall 12. Sufficient space exists between the inner arcuate surface of back wall 28 and outer heating unit wall 12 to permit an envelope 33 to be inserted therein and wrapped substantially completely around heating wall 12. Doors 29 and 30, which may be formed from rigid synthetic resinous plastic material, are secured in the closed position by latch 34 to prevent balloon-like expansion of envelope 33 from internal hydrostatic pressure of the blood or other liquid being warmed.

Figure 4:
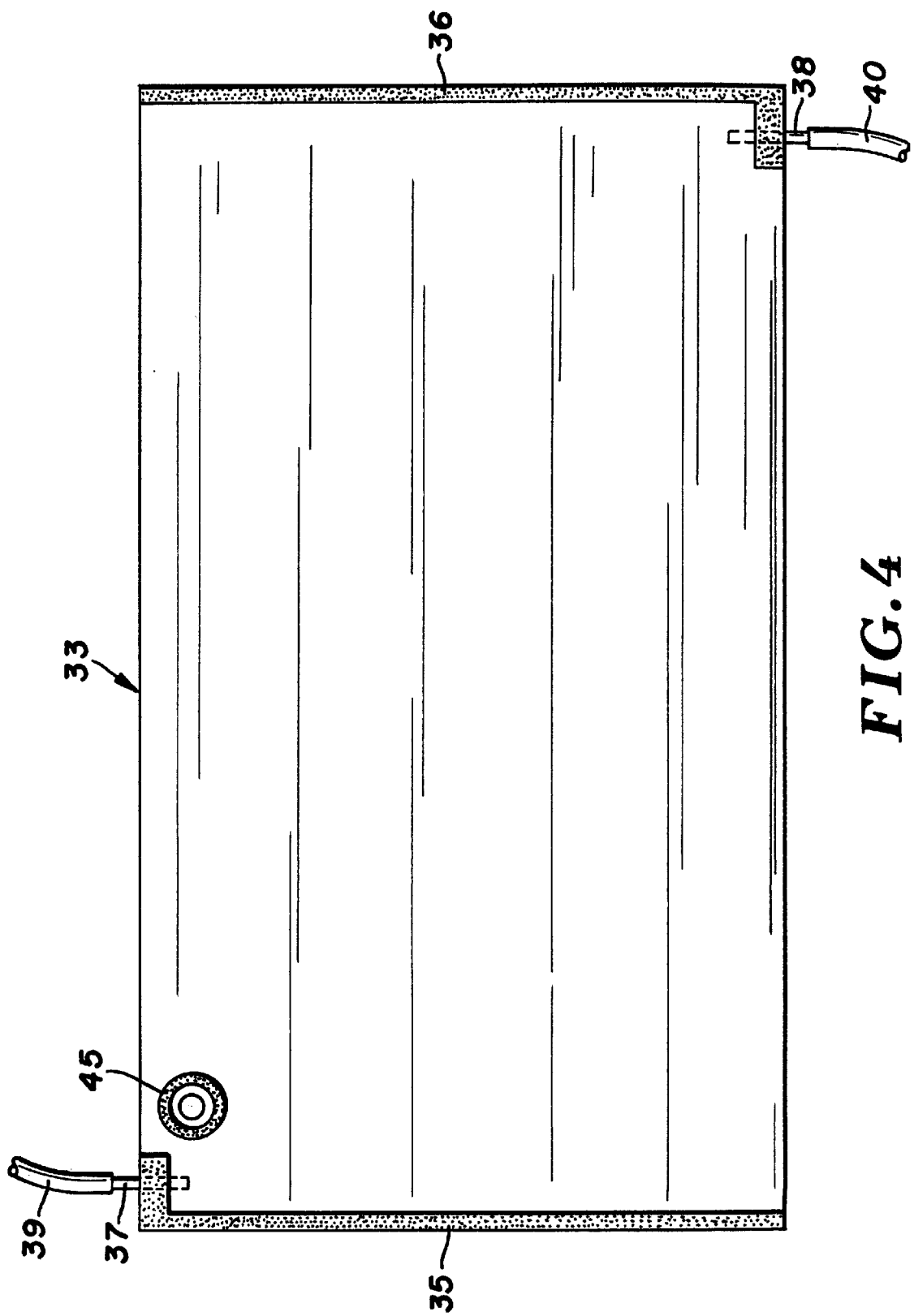
FIG. 4 is a front elevational view of one form of a disposable heat exchanging liquid warming envelope.

Envelope 33, as shown in FIG. 4, is generally similar to that shown in my U.S. Pat. No. 5,420,962. Envelope 33 is of a size to fit between outer heating unit wall 12 and the inner surfaces of housing back wall 28 and restraining doors 29 and 30. The envelope 33 is formed from thin flexible heat sealable synthetic resinous plastic sheet material such as 4 mil flat-lay polyethylene tubing. The end openings of the flat plastic tube are heat sealed at 35 and 36 to form left and right sealed end edges 35 and 36, respectively.

Relatively short inlet/outlet tubes 37 and 38, preferably polyethylene, are collar heat sealed between the two faces of the heat exchanging envelope closely adjacent to the left and right end edges 35 and 36, respectively. The inlet/outlet tubes 37 and 38 project outwardly from the top and bottom edges of the envelope, respectively. Both tubes extend a short distance within the envelope. Tubes 37 and 38 preferably have an inside diameter of about 1/8th to 1/4th inch.

A flexible liquid inlet/outlet tube 39 is press fit over tube 37 and a similar flexible tube 40 is press fit over tube 38. Tubes 37 and 38 are interchangeable as inlets or outlets depending upon whether the blood or other liquid to be warmed flows upwardly or downwardly through the liquid warmer.

In the embodiment shown the cold liquid enters tube 37 which extends through an opening 41 in the top of the heater which connects to an inlet header groove 42. The liquid causes the envelope to expand into the header groove which serves to distribute the liquid around the circumference of the external cylindrical heating surface 12. The liquid is warmed by convection as it flows in a thin layer within the envelope from inlet header groove 42 downward to outlet header groove 43 where it exits into outlet tubes 38 and 40 which extend through exit opening 44 connected to groove 43 at the bottom of the housing. Air bubbles escape through a vent adjacent to the top edge of the envelope provided with hydrophobic air filter 45.

The housing of fan 26 has a warmed air outlet duct 46 extending through the wall of housing base 11. A warm air hose 47 is connected to duct 46. Liquid delivery tube 40 is enclosed within hose 47. The hose 47 maintains the physiologic temperature of the warmed blood or other liquid in its passage between the heater unit and the patient to be transfused. Hose 47 is flexible and preferably made of a lightweight insulating material, such as a thin-walled corrugated collapsible plastic tube encased within a thin plastic sleeve sealed to each end of the corrugated tube and enclosing an insulating air space. Typically the corrugated tube may have an inside diameter of about 22 mm and the sleeve may be about 2 mil thick polyethylene with about a 4 inch circumference. Alternatively the air hose may be formed from closed cell polyethylene foam.

The outside wall of housing back wall 28 is provided with a bracket 48 supporting a hand screw 49 for engaging the post 50 of any standard IV stand.

In the operation of the system, cold blood or other liquid to be transfused enters the heat exchanging envelope 33 through inlet tube 37. The envelope is sandwiched between the outer cylindrical heating unit wall 12 and housing back wall 28 and doors 29 and 30. The heating unit is warmed by condensation of steam generated therein. The top edge of envelop 33 balloons slightly into inlet header groove 42 in the housing so that the liquid is evenly distributed around the cylindrical housing and flows in a thin layer to the bottom of the envelope where it collects in a slightly ballooned lower edge of the envelop in outlet header groove 43 from whence the warmed liquid flows outwardly into tube 40 to the patient. Concurrently, air drawn through the heater unit is warmed in its passage through the center of the heater unit, past fins 24 and into hose 47 for maintaining the temperature of the warm liquid until it enters the patient.

The system as described offers a number of advantages as compared to prior art blood warmers. The cylindrical heating unit structure is efficient again st pressure loading. Locating the electric foil element in the bottom of the heating unit allows use of a shallow reservoir producing more than 95% heating surface warmed by vapor. This compares favorably with flat heating units with etched foil heaters on the sides which have only about 75% vapor contact. The numbers of heaters, controllers and sensors are reduced by 50%.

It is apparent that many modifications and many variations of this invention as herein before set forth may be made without departing from the spirit and scope thereof. The specific embodiments described are given by way of example only and the invention is limited only by the terms of the appended claims.

I claim:

1. A system for warming blood or other liquids to body temperature for infusion into a patient, said system comprising:
    A) a blood warmer apparatus having a closed elongated annular cylindrical condensation heating chamber with an outer cylindrical heat exchanging wall and an inner spaced apart tubular heat exchanging wall, a cylindrical heat retaining shell closely spaced from and surrounding said heating chamber, and a flat flexible heat exchanging liquid warming envelope held clamped between the outer wall of said heating chamber and surrounding shell,
    B) a tubular air heating unit housed within the inner tubular wall of the heating chamber including:
        1) a cool air inlet at one end of said unit,
        2) a plurality of heat transfer fins extending longitudinally and radially inward from the inner tubular wall of the heating chamber,
        3) a fan for conducting air from said inlet past said fins, and
        4) a warmed air outlet from said housing,
    C) an external outer elongated air hose connected at one end to said warmed air outlet and extending to the patient, said air hose adapted to receive an inner elongated liquid flow line therein.

2. A system according to claim 1 where in said fan is located within a housing at the opposite end of said air heating unit from said air inlet.

3. A system according to claim 1 wherein said heating chamber includes a flat annular bottom wall having an electric etched foil heater element fixed thereto.

4. A system according to claim 1 wherein said cylindrical heat retaining shell includes a vertically extending back wall having an inner arcuate surface and a pair of arcuate doors hingedly connected thereto, said doors extending substantially completely around said heating chamber and being swingable outwardly to facilitate positioning of said envelope in the space between the heating chamber and shell.

5. A system according to claim 4 wherein a top header groove is provided in the inside surface of each of said doors closely spaced inward from the top edge thereof, and a bottom header groove is provided in the inside surface of each of said doors closely spaced inward from the bottom edge thereof.

6. A system according to claim 5 wherein an opening is provided in the top of said apparatus adjacent the outer perimeter thereof connecting with said top header groove and an opening is provided in the bottom of said apparatus adjacent the outer perimeter thereof connecting with said bottom header groove.

7. A system according to claim 6 wherein said liquid warming envelope is provided with a top inlet/outlet tube adjacent the top edge of the envelope, said tube extending through the opening at the top of the apparatus, and the warming envelope is provided with a bottom outlet/inlet tube adjacent the bottom edge of the envelope, said tube extending through the opening at the bottom of the apparatus and connected to an elongated flow line extending to the patient within said air hose.

8. A system according to claim 7 wherein said top inlet/outlet tube to said envelope is located adjacent one end of said envelope and the bottom outlet/inlet tube is located adjacent the opposite end thereof.

9. A system according to claim 1 wherein an air escape vent is provided adjacent the topmost edge of said envelope and a hydrophobic filter covers said vent.

10. A system according to claim 1 wherein said air hose is composed of a thin-walled corrugated collapsible synthetic resinous plastic tube encased within a thin synthetic resinous plastic sleeve sealed at each end to the corrugated tube.

11. A system according to claim 10 wherein said corrugated tube has an inside diameter of about 22 mm and said sleeve is composed of about 2 mil polyethylene tubing having a circumference of about 4 inches.

12. A system for warming blood or other liquids to body temperature for infusion into a patient, said system comprising:
  A) a blood warmer apparatus having:
    1) a closed elongated annular cylindrical condensation heating chamber with an outer cylindrical heat exchanging wall and an inner spaced apart tubular heat exchanging wall,
      a) said heating chamber having a flat annular bottom wall with an electric etched foil heater element fixed thereto,
    2) a cylindrical heat retaining shell closely spaced from and surrounding said heating chamber and including:
      a) a vertically extending back wall having a arcuate inner surface, and
      b) a pair of arcuate doors hingedly connected to said back wall, said doors extending substantially completely around said heating chamber and being swingable outwardly,
      c) a top header groove in the inner surface of each of said doors closely spaced inward from the top edge thereof,
      d) an opening in the top of said apparatus adjacent the outer perimeter thereof and connecting with said top header groove,
      e) a bottom header groove in the inner surface of each of said doors closely spaced inward from the bottom edge thereof,
      f) an opening in the bottom of said apparatus adjacent the outer perimeter thereof and connecting with said bottom header groove,
    3) a flat flexible heat exchanging liquid warming envelope held clamped between said outer wall of said heating chamber and surrounding shell and having
      a) a top inlet/outlet tube adjacent the top edge of said envelope and extending through the opening in the top of the apparatus, and
      b) a bottom outlet/inlet tube adjacent the bottom edge of said envelope and extending through the opening in the bottom of the apparatus,
  B) a tubular air heating unit housed within the inner tubular wall of the heating chamber including:
    1) a cool air inlet at one end of said unit,
    2) a plurality of heat transfer fins extending radially inward from the inner tubular wall of the heating chamber,
    3) a fan for conducting air from said inlet past said fins, and
    4) a warmed air outlet from said housing,
  C) an external outer elongated air hose connected at one end to said warmed air outlet and extending to the patient, said air hose adapted to receive an inner elongated liquid flow line from said envelope therein.

13. A system according to claim 12 wherein said top inlet/outlet tube to said envelope is located adjacent one end of said envelope and the bottom outlet/inlet tube is located adjacent the opposite end thereof.

14. A system according to claim 12 wherein said cool air inlet is located at the top end of said apparatus and said fan is located within a housing at the opposite end of said air heating unit from said air inlet.

15. A system according to claim 12 wherein said air hose is composed of a thin-walled corrugated collapsible synthetic resinous plastic tube encased within a thin synthetic resinous plastic sleeve sealed at each end to the corrugated tube.

16. A system according to claim 15 wherein said corrugated tube has an inside diameter of about 22 mm and said sleeve is composed of about 2 mil polyethylene tubing having a circumference of about 4 inches.

* * * * *